United States Patent
Troy (10) Patent No.: US 12,270,267 B2
(45) Date of Patent: Apr. 8, 2025

(54) METHODS AND SYSTEMS FOR ADJUSTING DRILLING FLUIDS

(71) Applicant: Robert W. Troy, Houston, TX (US)

(72) Inventor: Robert W. Troy, Houston, TX (US)

(*) Notice: Subject to any disclaimer, the term of this patent is extended or adjusted under 35 U.S.C. 154(b) by 0 days.

(21) Appl. No.: 18/916,595

(22) Filed: Oct. 15, 2024

(65) Prior Publication Data

US 2025/0075571 A1    Mar. 6, 2025

Related U.S. Application Data

(63) Continuation of application No. PCT/US2023/033268, filed on Sep. 20, 2023.

(Continued)

(51) Int. Cl.
*E21B 21/06* (2006.01)
*G01N 15/02* (2024.01)

(Continued)

(52) U.S. Cl.
CPC .......... *E21B 21/065* (2013.01); *G01N 15/02* (2013.01); *G01N 23/2076* (2013.01); *G01N 33/2823* (2013.01)

(58) Field of Classification Search
CPC .. E21B 21/065; G01N 15/02; G01N 23/2076; G01N 33/2823; G05B 23/0283;

(Continued)

(56) References Cited

U.S. PATENT DOCUMENTS

| 4,904,603 A | 2/1990 | Jones et al. |
| 5,306,909 A * | 4/1994 | Jones .................... E21B 49/005 250/339.11 |

(Continued)

FOREIGN PATENT DOCUMENTS

WO    2015156893 A1    10/2015

OTHER PUBLICATIONS

Matos, Taina, ISR for PCT/US2023/033268, Nov. 30, 2023, USPTO for WIPO, Alexandria, VA.

(Continued)

*Primary Examiner* — Mohammad K Islam
(74) *Attorney, Agent, or Firm* — Kearney, McWilliams & Davis; Erik J. Osterrieder (57) ABSTRACT

In one embodiment, the disclosure provides a method on a drilling fluid. The method may include acquiring data from each of a particle-size analyzer, x-ray fluorescence instrument, a mud check, and optionally an x-ray diffraction instrument, to yield acquired data for each of a plurality of drilling mud samples, wherein: (a) the particle size analyzer measures a plurality of drilling mud samples; (b) the x-ray fluorescence instrument and the x-ray diffraction instrument measure a mineral analysis of the plurality of drilling mud samples; and (c) the mud check measures properties of the plurality of drilling mud samples. Further, the method may include plotting a particle size distribution curve for at least one of the plurality of drilling mud samples, and calculating an amount of abrasive formation material(s) within at least one of the plurality of drilling mud samples. Further still, the method may include adjusting the drilling fluid.

26 Claims, 6 Drawing Sheets

Related U.S. Application Data (60) Provisional application No. 63/474,838, filed on Sep. 21, 2022.

(51) Int. Cl.
*G01N 23/207* (2018.01)
*G01N 33/28* (2006.01)

(58) Field of Classification Search
CPC ............... G05B 17/02; G05B 23/0221; G05B 23/0235; G05B 23/0264; G05B 2219/2642; G05B 23/024; G05B 23/0286; G05B 2219/2614; G05B 15/02
See application file for complete search history.

(56) References Cited

U.S. PATENT DOCUMENTS

| | | | | |
|---|---|---|---|---|
| 8,812,236 | B1* | 8/2014 | Freeman | E21B 21/065 73/152.43 |
| 8,877,064 | B2* | 11/2014 | Dixit | B01D 61/18 166/266 |
| 2007/0108201 | A1* | 5/2007 | Vinegar | C10L 3/08 219/770 |
| 2007/0284108 | A1* | 12/2007 | Roes | E21B 43/2401 166/302 |
| 2013/0192360 | A1 | 8/2013 | Jamison et al. | |
| 2017/0321546 | A1 | 11/2017 | Lawie et al. | |
| 2018/0100390 | A1* | 4/2018 | Patil | E21B 49/003 |
| 2018/0238774 | A1* | 8/2018 | Amendt | G01N 33/24 |
| 2020/0003599 | A1* | 1/2020 | Theuveny | G01F 1/74 |
| 2020/0386905 | A1* | 12/2020 | Mitchell | G01N 23/223 |
| 2022/0107279 | A1* | 4/2022 | Krumm | G01N 23/2055 |
| 2022/0145751 | A1* | 5/2022 | Liu | G01V 5/12 |

OTHER PUBLICATIONS

Matos, Taina, WO for PCT/US2023/033268, Nov. 30, 2023, USPTO for WIPO, Alexandria, VA.

Osterrieder, Erik J., Demand for PCT/US2023/033268, Jul. 22, 2024, KMD, Houston, TX.

Islam, Mohammad K., IPRP after Chapter II for PCT/US2023/033268, Oct. 3, 2024, USPTO for WIPO, Alexandria, VA.

* cited by examiner

```
XPowder
Max. counts: 208
Data file: C:\Users\btroy\Dropbox\Customer Tests\3.11.2021\processed
\PV_Fluid_HP629-ka.txt Kalpha1..: 1.54060

Kalpha2..:       1.54060
Kalpha...:       0.00000    Ka2/
Ka1..: 0.50000

Total/Average counts = 100722/101±89              48.374±42.838(%)
------------------------------------------------------------------------

XPowder
Max. counts: 400
Data file: C:\Users\btroy\Dropbox\Customer Tests\2022 Tests\9.9.2022\MS Directional\MS_Directional_MSMO_96430
\MS_Directional_MSMO_96430\processed\MS_Directi onal_MSMO_96430-ka.txt Kalpha1..:       1.78897
Kalpha2..:       1.79278
Kalpha...:       1.79024   Ka2/
Ka1..: 0.50000

Total/Average counts = 103284/103±92    25.769±23.082(%)
------------------------------------------------------------------------

------------------------------------------------------------------------
Quantitative section based on AMCSD cards
Sample= C:\Users\btroy\Dropbox\Customer Tests\2022 Tests\9.9.2022\MS Directional\MS_Directional_MSMO_96430
\MS_Directional_MSMO_96430\processed\MS_Directi onal_MSMO_96430-ka.txt
                     Card   I    Phase      I RIR   I%W Unc m/R IMu/rho I   %W Xtal   I %W Xtal+A ------------------------------------------------------------------------
01-0839  I Quartz= Si O2              I14.65 I 52.9(1.2) I0053.1 I 50.7(1.2) I42.7(1.0)

01-0153  I Calcite= Ca C O I11.04 I 08.8(3.7) I0096.1 I 09.0(3.7)   I07.6(3.1) 01-0215  I Barite= Ba S O4 I16.98 I
07.4(3.6) I0276.6 I 08.5(3.6)  I07.2(3.0)

01-3426  I Halite= Na Cl              I12.30 I 07.0(3.7) I0116.0 I 07.3(3.7) I06.2(3.2)

01-4686  I Gypsum= Ca S O6 I05.24 I 12.8(3.8) I0091.9 I 13.1(3.8)  I11.0(3.2)
01-9944  I Montmorillonite  I26.57 I 01.8(1.8) I0088.5 I 01.8(1.8)  I01.5(1.5)
010414 amorphous-stuff12  s I03.10 I 10.5(2.0) I0098.9 I 09.8(4.0) I106(3.0)) MS_Directional_MSMO_96430-ka: R-
according factor= 0.0894
Density= 1.000(g·cm-3)    µ/Dx of the mixture= 87.6 cm2·g-1
```

Figure 4

Mud Check Solids Characterization

| Sample Information | | Oil/Water Ratio | | Rheology | |
|---|---|---|---|---|---|
| Rig Name: | Rig 42 | Oil (%) | 79.9 % | FV | N/A sec/qt |
| Well Name: | | Water (%) | 20.1 % | PV | 38 cP |
| #2000H | | Oil/Brine Ratio | | YP | 13 lb/100ft² |
| Test | | Corrected Oil Content (%) | 78.5 % | Temp for PV | 150 deg F |
| Date: 9.7.2022 | | Brine Content (%) | 21.5 % | 600 RPM | 89 cP |
| MD (ft): | | Solids Analysis | | 300 RPM | 51 cP |
| Sample 2 | | Lo / Gravity Solids (vol%) | 18.90 vol% | 200 RPM | 37 cP |
| Source: | | High Gravity Solids (vol%) | 7.87 vol% | 100 RPM | 23 cP |
| Sample Date 8.31.2022 | | Corrected Solids (vol%) | 26.77 vol% | 6 RPM | 8 cP |
| | | Dissolved Solids (vol%) | 1.23 vol% | 3 RPM | 8 cP |
| Density | deg F | Total Retort Solids (vol%) | 28.00 vol% | Gels - 10 sec | 12 lb/100ft² |
| Mud Weight (lb/gal) | 12.50 lb/gal | SG of Whole Mud | 1.50 SG | Gels - 10 min | 20 lb/100ft² |
| High Gravity Solids - SG | 4.1 SG | Average SG of Solids | 3.08 SG | Gels - 30 min | lb/100ft² |
| Lo / Gravity Solids - SG | 2.65 SG | Salinity | | Remarks | |
| Base Oil Weight (lb/gal) | 7.0 lb/gal | Chlorides, Whole Mud (mg/l) | 30,000 mg/l | Sample #: | |
| Base Oil - SG | 0.84 SG | Water Phase Salinity (ppm) | 245,185 ppm | Vol. (bbl): | |
| Retort Values | | CaCl₂ (mg/l) | 47,100 mg/l | Time: | |
| Oil Content (vol%) | 57.5 vol% | CaCl₂ (lb/bbl) | 16.5 lb/bbl | Field MW: | |
| Water Content (vol%) | 14.5 vol% | CaCl₂ (Weight %) | 24.5 % | Tested by | ED |
| Chemical Properties | | Brine Content (vol%) | 15.7 vol% | Observed by | |
| Alkalinity (ml of H₂SO₄) | 5.4 ml | Brine Density - SG | 1.22 SG | | |
| Excess Lime (lb/bbl) | 7.0 lb/bbl | | | | |
| Calcium (mg/l) | 17,100 mg/l | | | | |
| Electric Stability (-abs) | 1,250 volts | | | | |
| HTHP Filtrate (ml) | ml/30 min | | | | |
| Cake Thickness, HTHP (1/32in) | 3 1/32 inch | | | | |

METHODS AND SYSTEMS FOR ADJUSTING DRILLING FLUIDS

REFERENCE TO RELATED APPLICATION

This is a continuation application, which claims priority to Patent Treaty Cooperation application number PCT/US23/33268 filed on Sep. 20, 2023 that claims priority to U.S. provisional patent application Ser. No. 63/474,838 filed on Sep. 21, 2022 that is hereby incorporated by this reference in its entirety.

FIELD

This disclosure generally relates to a methods and systems for using particle-size ("PSA"), mud check, and x-ray fluorescence ("XRF") analyses, and optionally x-ray diffraction ("XRD") analysis, in near time or real-time to measure the amount of abrasive mineral formations, e.g., quartz or sand, within a drilling fluid to make adjustments thereto and/or create a predictive analysis or forecast to create actions, which limit the wear on downhole drilling tools by removing low-gravity particles within a drilling fluid management system for improved well-drilling efficiency and mitigation or prevention of non-productive time, i.e., commonly known as lost time while drilling a well.

BACKGROUND

A need exists for reliable methods and systems to provide the percent of specific formation materials of the low-gravity solids (Drilled Solids) within a drilling fluid from a wellbore while being drilling to identify formation materials that have the ability to create wear on downhole tools, pipe, elastomers and other mechanical me mechanisms to include but not limited to metal, rubber gasket and other nonmetallic material.

Drilling fluid may contain only barite and other low-gravity particles, which are the rocks/minerals that the drilling fluid accumulates while drilling through various formation during the drilling operation. This disclosure on using x-ray fluorescence to indicate the formation of specific elements of abrasive formation materials, e.g., quartz rocks (a type of low-gravity solids) in the drilling fluid requiring dilution to reach a reduced level, certain level (percentage) of the within the drilling fluid to prevent damage to downhole and surface equipment drilling equipment. When all three are utilized together, they more fully optimize the drilling fluid for more efficient drilling.

Low Gravity Solids (LGS) properties are abrasive and can/will cause wear on drilling tools and downhole equipment. Quartz is an abrasive formation material of the LGS. One or more of the LGS minerals (Rocks) can cause equipment failure downhole by causing excess wear and downhole tool failure.

Bothe using XRF, x-ray diffraction ("XRD"), PSA, and mud check, one can optimize the drilling fluid to maximize drilling efficiency and properties and/or reduce costs.

BRIEF DESCRIPTION OF THE DRAWINGS

FIG. 3 is an example of an XRD analysis of a drilling fluid to measure the abrasive formation material within the low-gravity solids, e.g., silicate ($SiO_2$), barite ($BaSO_4$), etc.

DETAILED DESCRIPTION OF THE EMBODIMENTS

It is to be understood that the disclosed methods and systems are not limited to the particular embodiments and that it can be practiced or carried out in various ways.

Obtaining optimal drilling performance depends on (1) drilling a well as efficiently and at the minimal cost as practical; (2) eliminating time spent correcting drilling issues/problems such as non-productive time (NPT) and invisible lost time (ILT), which are mainly due to downhole tool and surface equipment failures as a result of abrasive drill solids with abrasive properties retained in the drilling fluid; (3) increasing safety by being able to better control the well and formation pressures to reduce formation damage; and (4) creating the capability to detect early or abnormal well conditions, thus being able to take corrective action and minimizing the probability of an uncontrolled flow from the well.

Drilling fluids are circulated into and out of the wellbore during the drilling process to (1) provide hydrostatic pressure against the formation to prevent formation fluids from entering the wellbore (i.e., controlling the well and preventing uncontrolled flow from entering the wellbore), (2) lubricate the drill bit thus keeping the drill bit cool and clean during drilling operations, and (3) carry drill cuttings out to the surface to be processed through the surface solids control equipment back to a proper particle size distribution and minimizing the effect of abrasive LGS on the surface and downhole tools to maximize drilling rate at the same time minimizing Non-Productive Time (NPT) by minimizing downhole tools' failure as a result of abrasive formation material, e.g., quartz ($SiO_2$) not being removed from the drilling fluid.

The methods and systems improve well control during drilling operations. Well control is important because blowouts can kill people. Blowouts have a severe environmental impact by polluting water, air, and land.

The methods and systems improve safety because fewer drilling days reduce accidents. Well accidents result in explosions which can cause death or injury to rig workers. Accidents also have a severe environmental impact by polluting water, air, and land.

The methods and systems reduce the number of days required to drill wells by reducing the impact of surface equipment and downhole tool failure. Reducing the numbers of days reduces costs. This results in increased supply which in turn reduces the cost of oil and gas products to the consumer.

The methods and systems decrease the number of contaminated drilling fluids produced. Contaminated drilling fluids must be treated and disposed of. The treatment and disposal pollute the water and land.

The methods and systems have high-economic benefits to the operator to allow the recovery of additional reserves for production by allowing more wells to be drilled with the same dollars.

The methods and systems enable ultra-extended reach drilling, reliable and efficient drilling operations in difficult environments including offshore and deep-water applications, and generates cost reduction, safety, and operational improvements throughout the drilling operations.

Drilling fluids are often referred to in the drilling industry as "mud."

Drilling fluids are composed of water, solids, additive chemicals, other additives, and occasionally a percentage of diesel or other hydrocarbon-based fluids.

Drilling fluids can contain weighting agents (i.e., particles) to create the hydrostatic head (pressure required to counterbalance the formation pressure) to prevent the formations from creating an uncontrolled flow into the wellbore and a loss of well control.

Weighting agents are additives to drilling fluids that are typically suspended in the drilling fluid used to increase the density and ultimately increase the hydrostatic pressure needed to balance equally formation pressures (i.e., balance drilling).

Solids control equipment is used at the drilling rig to separate the drilling cuttings (formation mineralogy) from the drilling fluids that are generated at the drill bit and carried to the surface for separation.

Solid control equipment can include a mud tank, shale shaker, vacuum degasser, desander, desilter, hydro cyclones, centrifuges, and other equipment.

Drilling fluid measurements can include XRF and XRD to measure the mineralogy of the geological formations elements by percentage e.g., the percentage of silicate in the quartz.

When all four technologies and measurements are utilized together, i.e., XRF, XRD, PSA and Mud Check, the entire solids control equipment package has the ability to create the proper particle size distribution for the drilling fluid within a well and maintain the minimum abrasiveness of the fluid on downhole equipment to prevent failures.

Chemicals (e.g., salt, clay, barite, lime, and emulsifier) can be added to the drilling fluids after passing through the solids control equipment and before the drilling fluids are returned to the wellbore to obtain the proper weighting of the drilling mud and obtaining the proper particle size distribution curve for increased drilling efficiency.

The methods and systems address a newly discovered area of improving drilling efficiency by optimizing current drilling fluids best practices to create suitable particle size distributions (PSD) for the drilling fluid throughout the drilling process.

Particle size analysis (PSA) is the process to determine the size range and average or mean size of particles in a drilling fluid sample.

XRF (X-ray fluorescence) is a non-destructive analytical technique used to determine the elemental composition of materials. XRF analyzers determine the chemistry of a sample by measuring the fluorescent (or secondary) X-ray emitted from a sample when it is excited by a primary X-ray source. Quantitative XRF data informs the user as to the absolute quantity of an element present in a sample. Calibrations are made by using samples with known concentrations of elements of interest to create a calibration curve that relates the specifically known concentrations to peak heights.

XRD (X-RAY Diffraction) is a non-destructive method to identify material relies on the wave/particle nature of X-rays to obtain information about the structure of crystalline material. Primary use of the technique is the identification and characterization of compounds based on their diffraction pattern.

Calculation of pound per barrel of a specific formation LGS or mineral from an X-ray Diffraction measurement may be accomplished such as by the following example: X-ray Diffraction measurement material you sent in has 10.3% SiO2 by weight. That means that out of 100 lbs., 10.3 lbs. will be $SiO_2$. All LGS are assumed be 2.6 specific gravity per API. Therefore if the volume percent LGS is known, the lb/barrel of LGS is calculated by (Vol. Percent LGS)×(910.7 lb/bbl)=lb LGS in one barrel. The 910 comes from 2.6×8.34×42 which is what a barrel would weigh if you could pack it 100% full of drill solids.

The dominant effect that occurs when an incident beam of monochromatic X-rays interacts with a target material is scattering of those X-rays from atoms within the target material. In materials with regular structure (i.e., crystalline), the scattered X-rays undergo constructive and destructive interference. This is the process of diffraction. The diffraction of X-rays by crystals is described by Bragg's Law, n(lambda)=2d sin(theta). The directions of possible diffractions depend on the size and shape of the unit cell of the material. The intensities of the diffracted waves depend on the kind and arrangement of atoms in the crystal structure. However, most materials are not single crystals, but are composed of many tiny crystallites in all possible orientations called a polycrystalline aggregate or powder. When a powder with randomly oriented crystallites is placed in an X-ray beam, the beam will see all possible interatomic planes. If the experimental angle is systematically changed, all possible diffraction peaks from the powder will be detected.

While the maximum particle size for the particle size distribution curve should not be greater than 6 microns, however, a maximum particle size for the particle size distribution of less than approximately 12 microns will still greatly increase the efficiency of the well drilling and reduce costs.

Adding the use of the particle size distribution curves for the drilling fluids to current best practices for drilling a well results in a 20 percent improvement in drilling.

Current industry emphasis on drilling efficiency is not on optimizing the particle-size distribution curve, but rather on (1) removing drilling cuttings or (2) adding or removing ingredients from the drilling fluids.

Current drilling industry practice does not utilize particle size analysis for drilling fluid management. Conventional drilling practices typically focus on increasing drilling rates to attempt to increase drilling efficiency.

Standard drilling fluid practices are based upon analyzing the drilling fluids a few to several times a day and do not include particle size analysis.

Current best practices modify the chemical composition of drilling fluids (1) by adding or removing other chemicals during the drilling process; (2) by removing drilling cuttings; or (3) by adding base fluid.

In addition to non-productive time and invisible lost time, poor drilling fluid properties, due to include abrasiveness of the low gravity particles within the fluid and fluid maintenance result in (1) poor drilling efficiency, (2) excessive use of base fluid chemicals, (3) drill bit wear, (4) excess/unnecessary contaminated waste to be disposed, (5) drilling performance problems such as stuck pipe, and (6) circulation issues such as uncontrolled flow into or from the formation.

The methods and systems may create at least a 20 percent increase in capital efficiency which contributes directly to the profitability of the oil and gas drilling company. Thus, the methods and systems enable oil and gas producers to drill more wells for the same cost, that is, for the cost of drilling 100 wells, 120 can now be drilled for the same cost. This enables oil and gas producers to improve company net revenue, improve the return on investment, and ultimately improve the share price if the company is a publicly traded company.

Embodiments of the methods and systems may significantly reduce the amount of unnecessary contaminated drilling fluids and the associated transportation and disposal costs.

Embodiments of the methods and systems may reduce the number of days required to drill in extreme or fragile environments (i.e., deep-water, the arctic, or by fracking) resulting in reducing the risk to safety and/or environmental hazards and accidents.

When utilizing conventional industry practice, the finer particulates (i.e., still particles but small ones) increase the plastic viscosity defined as the force required to initiate fluid flow relative to the amount, size, and shape of the particles in suspension in the drilling mud.

Generally, as particle sizes become finer due to mechanical/chemical degradation, the particle-size distribution shows an increase of finer solids and reduction of coarser solids.

The plastic viscosity can increase; however, finer distributions of more inert solids less than 6 microns (such as: weighting agents such as barite, hematite) should not cause dramatic increases in plastic viscosity as reactive solids will. This allows for higher concentrations of inert solids without the same negative effects on plastic viscosity as seen using reactive solids.

From the analysis of the XRF, XRD, Mud Check, and particle size distribution curve of the drilling fluids and drilling fluid properties, corrective actions to the drilling fluid's percentage of low-gravity solids, which contain abrasive material, can be identified and corrected through the use of solids control equipment and dilution.

Based on the analysis of the drilling fluids composition (Mud Check), XRF, XRD and particle size distribution, the drilling fluid is decontaminated (removal of drilling cuttings and unwanted particle sizes, low gravity solids that contain abrasive material) throughout the drilling process by processing the drilling fluid through the solid control equipment to separate and remove particles to meet the desired particle size distribution and minimize the amount low gravity solids that contain abrasive material e.g., quartz, for optimal drilling efficiency prior to the drilling fluid being allowed to return to the wellbore. Drilling efficiency can refer to various monitored parameters which can include, but are not limited to, the following: drill bit penetration, well control, and reduction of non-productive time or invisible lost time during drilling operations.

Fluid properties during the optimization process are to be maintained in accordance with standard industry practices to include but not limited to density, viscosity, plastic viscosity, yield point, salinity, alkalinity, electric stability, hardness, gel strength, oil/water ratio, corrected solids, total solids, and cake thickness.

The methods and systems, in conjunction with using the current inputs from the drilling rig (e.g., mud weight and current drilling penetration rate), may determine the best possible corrective actions, such as modifying the drilling fluids, adjusting solids control equipment parameters, or modifying the drilling program/parameters.

The methods and systems in part use a system that when utilized properly with solids control equipment may create a continuous improvement loop to continually optimize the drilling fluid's particle size distribution and percentage of abrasive material within the low gravity solids to prevent downhole wear. The knowledge system includes a set of rules in the data storage of the administrative processor used by the methods and systems.

The invention, when utilized along with best industry practices for the drilling fluid, will formulate and present to a user the corrective actions necessary utilizing the solids control equipment to create the optimal particle size distribution for the drilling fluid.

Although drilling fluids are most often associated with oil and gas applications, drilling fluids are used in any application of drilling through the Earth's formation for a well to include but not limited to drilling water wells, hydrothermal wells, or wells to deposit high level nuclear waste.

The following definitions are used herein:

The term "about" means the number itself and/or within 5% of the stated number. For instance, with about 5%, this means 5 and/or any number or range within the range of 4.75 to 5.25, e.g., 4.75 to 4.96, 4.81 to 5.1, etc.

The term "alkalinity" as used herein refers to a chemical property of an aqueous system that implies that there are more hydroxyl ions (OH—) in the system, or a potential to produce more hydroxyl ions, than there are hydrogen ions (H+), or potential to produce hydrogen ions.

The term "barite" as used herein refers to a dense mineral comprising barium sulfate [$BaSO_4$]. Commonly used as a weighting agent for all types of drilling fluids, barites are mined in many areas worldwide and shipped as ore to grinding plants in strategic locations. Contaminants in barite, such as cement, siderite, pyrrhotite, gypsum, and anhydrite, can cause problems in certain mud systems and should be evaluated in any quality assurance program for drilling-mud additives.

The term "chloride ion" is the anion $Cl^-$. It is formed when the element chlorine gains an electron or when a compound such as hydrogen chloride is dissolved in water or other polar solvents. Chloride salts such as sodium chloride are often very soluble in water and are part of proper drilling fluid maintenance.

The term "borehole or wellbore" as used herein refers to an open hole or uncased portion of the well. Borehole can refer to the inside diameter of the wellbore wall, the rock face that bounds the drilled hole.

The term "cake thickness" refers to the measurement of the thickness of the filter cake, usually recorded in 1/32 of an inch. Under dynamic conditions, filter-cake thickness depends on rate of deposition versus erosion caused by fluid circulation and mechanical abrasion by the rotating drill string. Typically, the filter cake will reach an equilibrium thickness in the wellbore. In laboratory tests, however, filter cake is built under static conditions with no erosion.

The term "centrifuge" as used herein refers to an item of solids-removal equipment that removes fine and ultrafine solids. It consists of a conical drum that rotates at 2000 rpm to 4000 rpm. Drilling fluid is fed into one end and the separated solids are moved up the bowl by a rotating scroll to exit at the other end. Centrifuges generally have limited processing capacity (50 gpm to 250 gpm) but are useful for processing weighted drilling fluids and can remove finer solids than can a hydrocyclone or shaker screens. They can also be used for water clarification or for processing oily cuttings.

The term "centrifuge interface" refers to information input into a database in the administrative data storage that includes manufacturer name, model number, gravity force, time stamp, and date stamp.

The term "client device" refers to a computer, a laptop, a tablet, a smartphone, or other device with a processor or ability for bi-directional data communication.

The term "consist essentially of" means about 95% or more.

The term "cut point" refers to the minimum point of mechanical separation for a given particulate removal device.

The term "density" refers to a unit of mass per unit of volume. Density is typically reported in $g/cm^3$ (for example, rocks) or pounds per barrel (drilling mud) in the oil field. High Gravity Solids (HGS) are at or near 4.2 specific gravity while Low Gravity Solids (LGS) are at or near 2.6 specific gravity.

The term "drill bit" as used herein refers to a tool used to crush or cut rock. Everything on a drilling rig directly or indirectly assists the bit in crushing or cutting the rock. The bit is on the bottom of the drill string and must be changed when it becomes excessively dull or stops making progress. Most bits work by scraping or crushing the rock, or both, usually as part of a rotational motion. Some bits, known as hammer bits, pound the rock vertically in much the same fashion as a construction site air hammer.

The term "drill pipe" refers to a tubular steel conduit fitted with special threaded ends called tool joints. The drill pipe connects the rig surface equipment with the bottom hole assembly and the bit, both to pump drilling fluid to the bit and to be able to raise, lower and rotate the bottom hole assembly and bit.

The term "drilling fluid" refers to any of a number of liquid and gaseous fluids and mixtures of fluids and solids (as solid suspensions, mixtures and emulsions of liquids, gases, and solids) used in operations to drill boreholes into the earth. Synonymous with "drilling mud" in general usage, although some prefer to reserve the term "drilling fluid" for more sophisticated and well-defined "muds." Classifications of drilling fluids have been attempted in many ways, often producing more confusion than insight. One classification scheme, given here, is based only on the mud composition by singling out the component that clearly defines the function and performance of the fluid: (1) water-base, (2) non-water-base, and (3) gaseous (pneumatic). Each category has a variety of subcategories that overlap with each other.

The term "drilling rig" refers to the machine used to drill a wellbore. In onshore operations, the rig includes virtually everything except living quarters. Major components of the rig include the mud tanks, the mud pumps, the derrick or mast, the draw works, the rotary table or top drive, the drill string, the power generation equipment and auxiliary equipment. Offshore, the rig includes the same components as onshore, but not those of the vessel or drilling platform itself. The rig is sometimes referred to as the drilling package, particularly offshore.

The term "emulsifier" refers to a chemical additive that creates an emulsion, a dispersion of one immiscible liquid into another, by reducing the interfacial tension between the two liquids to achieve stability. Two emulsion types are used as muds: (1) oil-in-water (or direct) emulsion, known as an "emulsion mud" and (2) water-in-oil (or invert) emulsion, known as an "invert emulsion mud." The former is classified as a water-based mud and the latter as an oil-based mud.

The term "fine solids" or "fines" refers to the size of solids below the cut point of screens.

The term "ultrafines" refers to the size of solids below the cut point of solids equipment control which utilizes centrifugal force.

The term "fluid loss" refers to a leakage of the liquid phase of drilling fluid, slurry or treatment fluid containing solid particles into the formation matrix. The resulting buildup of solid material or filter cake may be undesirable, as may the penetration of filtrate through the formation. Fluid-loss additives are used to control the process and avoid potential reservoir damage.

The term "gravity force" or "gravity" refers to the force exerted measured by the earth's gravitational field, or the attractive force produced by the mass of the earth. Variations in the gravitational field can be used to map changes in the density of formations in the earth. Solids control equipment uses gravity force to separate particles suspended in fluid.

The term "hematite" as used herein refers to the mineral form of ferric oxide [$Fe_2O_3$]. The hematite ore used as a weighting material in drilling muds has a mica-like crystal structure that grinds to particle size suitable for use in drilling fluids. To check for potential wear, an abrasion test is usually run on hematite as a quality-control pilot test.

The term "high gravity solids" refers to dense solids, such as barite or hematite, which are added to a mud to increase its density, also known as weighting material. The concentration of high-gravity solids in weighted mud is measured by the mud engineer daily using mud weight, retort data, chloride titration data and other information. Solids are reported as lb/bbl or volume percent. The specific gravity of water is 1.00, barite is 4.20, and hematite 5.505 $g/cm^3$. Drill solids and other low-gravity solids are normally assumed to be 2.60 $g/cm^3$.

The term "lithology" refers to the composition or type of rock and their characteristics.

The term "low gravity solids" refers to a type of drilling-fluid solid having a lower density than barite or hematite, including drill solids and mud additives not including weighting agents. The mud engineer calculates the concentration of these and other types of solids on the basis of mud weight, retort analysis, chloride titrations and other information. Solids are reported as lb/bbl or volume percent. Water is 1.0, barite 4.20, and hematite 5.505 $g/cm^3$. Low-gravity solids are normally assumed to have a density of 2.60 $g/cm^3$.

The term "low specific gravity solids" refers a type of drilling-fluid solid having a lower density than the barite or hematite that is used to weight up a drilling fluid, including drill solids plus the added bentonite clay. The mud engineer calculates the concentration of these and other types of solids on the basis of mud weight, retort analysis, chloride titrations and other information. Solids are reported as lb/bbl or volume percent. Water is 1.0, barite 4.20, and hematite 5.505 $g/cm^3$. Low-gravity solids are normally assumed to have a density of 2.60 $g/cm^3$.

The term "measured depth" refers to the length of the wellbore, as if determined by a measuring stick. This measurement differs from the true vertical depth of the well in all but vertical wells. Since the wellbore cannot be physically measured from end to end, the lengths of individual joints of drill pipe, drill collars and other drill string elements are measured with a steel tape measure and added together. Importantly, the pipe is measured while in the derrick or laying on a pipe rack, in an intentioned, unstressed state. When the pipe is screwed together and put into the wellbore, it stretches under its own weight and that of the bottom hole assembly. Although this fact is well established, it is not considered when reporting the well depth. Hence, in virtually all cases, the actual wellbore is slightly deeper than the reported depth.

The term "mechanical separation" refers to physically separating solids suspended in a fluid using centrifugal force or screens.

The term "mud" refers to a drilling fluid that is transferred downhole, especially fluids that contain significant amounts of suspended solids, emulsified water or oil. Mud includes all types of water-bases, oil-based and synthetic-based drilling fluids. Drill-in, completion, and workover fluids are sometimes called muds, although a fluid that is essentially free of solids is not strictly considered mud.

The term "mud additive" refers to a material added to a drilling fluid to perform one or more specific functions, such as a weighting agent, viscosifier, or lubricant.

The term "mud pump" refers to a mud pump is a large reciprocating pump used to circulate the mud (drilling fluid) on a drilling rig. It is an important part of the oil well drilling equipment.

The term "mud report" refers to the report sheets filled out by the mud engineer at the well site on a daily basis. The mud report supplies results of tests performed several times per day as well as details about mud product usage, inventory, recommendations, and other pertinent information. Multiple-copy forms in a format approved by the American Petroleum Institute (API), which are provided by the mud service company, are the traditional type of mud report. Today, mud reports are more likely to be computerized and transmitted electronically.

The term "mud weight" refers to the mass per unit volume of a drilling fluid, synonymous with mud density. Weight is reported in lb/gal (also known as ppg), $kg/m^3$ or $g/cm^3$ (also called specific gravity or SG), $lb/ft^3$ or in hydrostatic gradient, $lb/in^2/ft$ (psi/ft) or pptf (psi/1000 ft). Mud weight controls hydrostatic pressure in a wellbore and prevents unwanted flow into the well. The weight of the mud also prevents collapse of casing and the open hole. Excessive mud weight can cause lost circulation by propagating, and then filling, fractures in the rock. Mud weight (density) test procedures using a mud balance have been standardized and published by the American Petroleum Institute.

The term "particle size analyzer" refers to a specialized piece of equipment to conduct analysis on samples or sample streams to determine the size and distribution of particles within that sample.

The term "particle size distribution" refers to the weight, or net volume, of solid particles that fall into each of the various size ranges, given as a percentage of the total solids of all sizes in the sample of interest. Particle size can be determined by sieve analysis, light scattering, passage through an electrically charged orifice, settling rate or other methods. Data are typically shown as a histogram chart with percentage-smaller-than on the y-axis and size ranges on the x-axis. Mud engineers use such data to operate solids-control equipment effectively. Particle size distributions are used to evaluate bridging materials for drill-in and completion fluids. Barite and hematite samples are examined to ensure performance without excessive wear on equipment and as an American Petroleum Institute/International Standards Organization (API/ISO) quality specification.

The term "particulate removal device" refers to at least one shaker receiving used drilling mud from the wellbore, and at least one centrifuge fluidly connected to a drilling mud pit that receives drilling mud with at least some particulates removed by at least one shaker.

The term "penetration rate" refers to the speed at which the drill bit can break the rock under it and thus deepen the wellbore. This speed is usually reported in units of feet per hour or meters per hour.

The term "rate of penetration" refers to the speed at which the drill bit can break the rock under it and thus deepen the wellbore. This speed is usually reported in units of feet per hour or meters per hour.

The term "reactive solids" refers to commercial additives, drilled solids, and clays that react vigorously to moisture and other substances. Also are consider abrasive and will cause wear on surface and downhole equipment if not properly maintained.

The term "real time data" refers to measurements-while-drilling (MWD) and logging while drilling, the data transmitted to surface shortly after being recorded.

The term "retention time" refers to an amount of time a liquid stays in a vessel. The retention time assures that equilibrium between the liquid and gas has been reached at separator pressure. The retention time in a separator is determined by dividing the liquid volume inside the vessel by the liquid flow rate. The retention time usually varies from 30 seconds to 3 minutes. If a foaming crude is present, the retention time can be increased by four times its normal values.

The term "rheology" refers to deformation and flow of matter. Rheology is an extremely important property of drilling muds, drill-in fluids, workover and completion fluids, cements and specialty fluids and pills. Mud rheology is measured on a continual basis while drilling and adjusted with additives or dilution to meet the needs of the operation. In water-based fluids, water quality plays an important role in how additives perform. Temperature affects behavior and interactions of the water, clay, polymers and solids in a mud. Downhole pressure must be considered in evaluating the rheology of oil muds.

The term "rotary table" refers to the revolving or spinning section of the drill floor that provides power to turn the drill string in a clockwise direction (as viewed from above). The rotary motion and power are transmitted through the kelly bushing and the kelly to the drill string. When the drill string is rotating, the drilling crew commonly describes the operation as simply, "rotating to the right," "turning to the right," or, "rotating on bottom." Almost all rigs today have a rotary table, either as primary or backup system for rotating the drill string. Top drive technology, which allows continuous rotation of the drill string, has replaced the rotary table in certain operations. A few rigs are being built today with top drive systems only, and lack the traditional kelly system.

The term "salinity" refers to a saltiness or dissolved salt content.

The term "salt" refers to the product formed by neutralization of an acid and a base. The term is more specifically applied to sodium chloride. Neutralization is an important reaction in many aspects of mud control and treatment.

The term "sample source" refers to a drilling mud sample as collected from a shaker, a centrifuge after being treated by a shaker, or a drilling mud sample as collected from a suction pit after being treated sequentially by a shaker and a centrifuge.

The term "shaker" refers to shale shaker, the primary and probably most important device on the rig for removing drilled solids from the mud. This vibrating sieve is simple in concept, but a bit more complicated to use efficiently. A wire-cloth screen vibrates while the drilling fluid flows on top of it. The liquid phase of the mud and solids smaller than the wire mesh pass through the screen, while larger solids are retained on the screen and eventually fall off the back of the device and are discarded. Obviously, smaller openings in the screen clean more solids from the whole mud, but there is a corresponding decrease in flow rate per unit area of wire cloth. Hence, the drilling crew should seek to run the screens (as the wire cloth is called), as fine as possible, without dumping whole mud off the back of the shaker. Where it was once common for drilling rigs to have only one or two shale shakers, modern high-efficiency rigs are often fitted with four or more shakers, thus giving more area of wire cloth to use, and giving the crew the flexibility to run increasingly fine screens.

The term "shaker interface" refers to information input into a database in the administrative data storage that includes manufacturer name, model number, first shaker screen, second shaker screen, third shaker screen, fourth shaker screen, time stamp, and date stamp.

The term "shale shaker" refers to a vibrating sieve and is simple in concept, but a bit more complicated to use efficiently. A wire-cloth screen vibrates while the drilling fluid flows on top of it. The liquid phase of the mud and solids smaller than the wire mesh pass through the screen, while larger solids are retained on the screen and eventually fall off the back of the device and are discarded. Smaller openings in the screen clean more solids from the whole mud, but there is a corresponding decrease in flow rate per unit area of wire cloth. Therefore, the drilling crew should seek to run the screens (as the wire cloth is called), as fine as possible, without dumping whole mud off the back of the shaker. Where it was once common for drilling rigs to have only one or two shale shakers, modern high-efficiency rigs are often fitted with four or more shakers, thus giving more area of wire cloth to use, and giving the crew the flexibility to run increasingly fine screens.

The term "shear rate" refers to the velocity gradient measured across the diameter of a fluid-flow channel, be it a pipe, annulus or other shape. Shear rate is the rate of change of velocity at which one layer of fluid passes over an adjacent layer. As an example, consider that a fluid is placed between two parallel plates that are 1.0 cm apart, the upper plate moving at a velocity of 1.0 cm/sec and the lower plate fixed. The fluid layer at the lower plate is not moving and the layer nearest the top plate is moving at 1.0 cm/sec. Halfway between the plate, a layer is moving at 0.5 cm/sec. The velocity gradient is the rate of change of velocity with distance from the plates. This simple case shows the uniform velocity gradient with shear rate (v1−v2)/h=shear rate=(cm/sec)/(cm/l)=l/sec. Hence, shear rate units are reciprocal seconds.

The term "shear stress" refers to the force per unit area required to sustain a constant rate of fluid movement. Mathematically, shear stress can be defined as: if a fluid is placed between two parallel plates space 1 cm apart and a force of 1 dyne is applied to each square centimeter of the upper plate to keep it in motion, the shear stress in the fluid is 1 dyne/cm squared at any point between the two plates.

The term "solids control equipment" refers to equipment used within a solid control system which includes: the mud tank, shale shaker, vacuum degasser, desander, desilter, and centrifuge.

The term "standpipe" refers to a rigid metal conduit that provides the high-pressure pathway for drilling mud to travel approximately one-third of the way up the derrick, where it connects to a flexible high-pressure hose (kelly hose). Many large rigs are fitted with dual standpipes so that downtime is kept to a minimum if one standpipe requires repair.

The term "true vertical depth" refers to the vertical distance from a point in the well (usually the current or final depth) to a point at the surface, usually the elevation of the rotary kelly bushing (RKB). This is one of two primary depth measurements used by the drillers, the other being measured depth. True vertical depth is important in determining bottom hole pressures, which are caused in part by the hydrostatic head of fluid in the wellbore. For this calculation, measured depth is irrelevant and true vertical depth must be used. For most other operations, the driller is interested in the length of the hole or how much pipe will fit into the hole. For those measurements, measured depth, not true vertical depth, is used. While the drilling crew should be careful to designate which measurement they are referring to, if no designation is used, they are usually referring to measured depth. Note that measured depth, due to intentional or unintentional curves in the wellbore, is always longer than true vertical depth.

The term means "substantially free" something is largely, but not wholly, absent, i.e., trace amounts may or may not be present.

The term "viscosifiers" refers to material in the drilling mud that alters its viscosity. Viscosity is defined as a property of fluids and slurries that indicates their resistance to flow, defined as the ratio of shear stress to shear rate. Viscosity can be expressed mathematically as follows: poise is the unit for viscosity, equivalent to dyne-sec/cm$^2$. Because one poise represents a high viscosity, $1/100$ poise, or one centipoise (cp), is used for mud measurements. One centipoise equals one millipascal-second. Viscosity must have a stated or an understood shear rate in order to be meaningful. Measurement temperature also must be stated or understood.

The term "viscosity" refers to a property of fluids and slurries that indicates their resistance to flow, defined as the ratio of shear stress to shear rate. Viscosity can be expressed mathematically as follows: poise is the unit for viscosity, equivalent to dyne-sec/cm$^2$. Because one poise represents a high viscosity, $1/100$ poise, or one centipoise (cp), is used for mud measurements. One centipoise equals one millipascal-second. Viscosity must have a stated or an understood shear rate in order to be meaningful. Measurement temperature also must be stated or understood.

The term "weighting agents" refers to weighting material, a high-specific gravity and finely divided solid material used to increase density of a drilling fluid. (Dissolved salts that increase fluid density, such as calcium bromide in brines, are not called weighting materials.) Barite is the most common, with minimum specific gravity of 4.20 g/cm$^3$. Hematite is a more dense material, with minimum specific gravity of 5.05 g/cm$^3$, per American Petroleum Institute (API) and International Standards Organization (ISO) specifications. Calcium carbonate, specific gravity 2.7 to 2.8, is considered weighting material but is used more for its acid solubility than for density. Siderite, specific gravity around 3.8, has been used to densify mud, but can cause problems by dissolving into the mud at high pH. Ilmenite, specific gravity of 4.6 has been used in drilling fluid and cement. Only barite and hematite have American Petroleum Institute/International Standards Organization (API/ISO) standards.

The term "weighting materials" refer to high-specific gravity and finely divided solid material used to increase density of a drilling fluid. (Dissolved salts that increase fluid density, such as calcium bromide in brines, are not called weighting materials.) Barite is the most common, with minimum specific gravity of 4.20 g/cm$^3$. Hematite is a more dense material, with minimum specific gravity of 5.05 g/cm$^3$, per American Petroleum Institute (API) and ISO specifications.

Calcium carbonate, specific gravity 2.7 to 2.8, is considered weighting material but is used more for its acid solubility than for density. Siderite, specific gravity around 3.8, has been used to densify mud, but can cause problems by dissolving into the mud at high pH. Ilmenite, specific gravity of 4.6 has been used in drilling fluid and cement. Only barite and hematite have American Petroleum Institute/International Standards Organization (API/ISO) standards.

The term "well control" refers to focused on maintaining pressure on open formations (exposed to the wellbore) to prevent or direct the flow of formation fluids into the wellbore. This technology encompasses the estimation of formation fluid pressures, the strength of the subsurface formations and the use of casing and mud density to offset those pressures in a predictable fashion. Also included are operational procedures to safely stop a well from flowing should an influx of formation fluid occur. To conduct well-control procedures, large valves are installed at the top of the well to enable well site personnel to close the well if necessary.

The term "wellbore" refers to the drilled hole or borehole, including the open hole or uncased portion of the well. Borchole can refer to the inside diameter of the wellbore wall, the rock face that bounds the drilled hole.

The term "yield point" refers to the ability of a drilling fluid to carry drilled cuttings to the surface.

Figure 1:
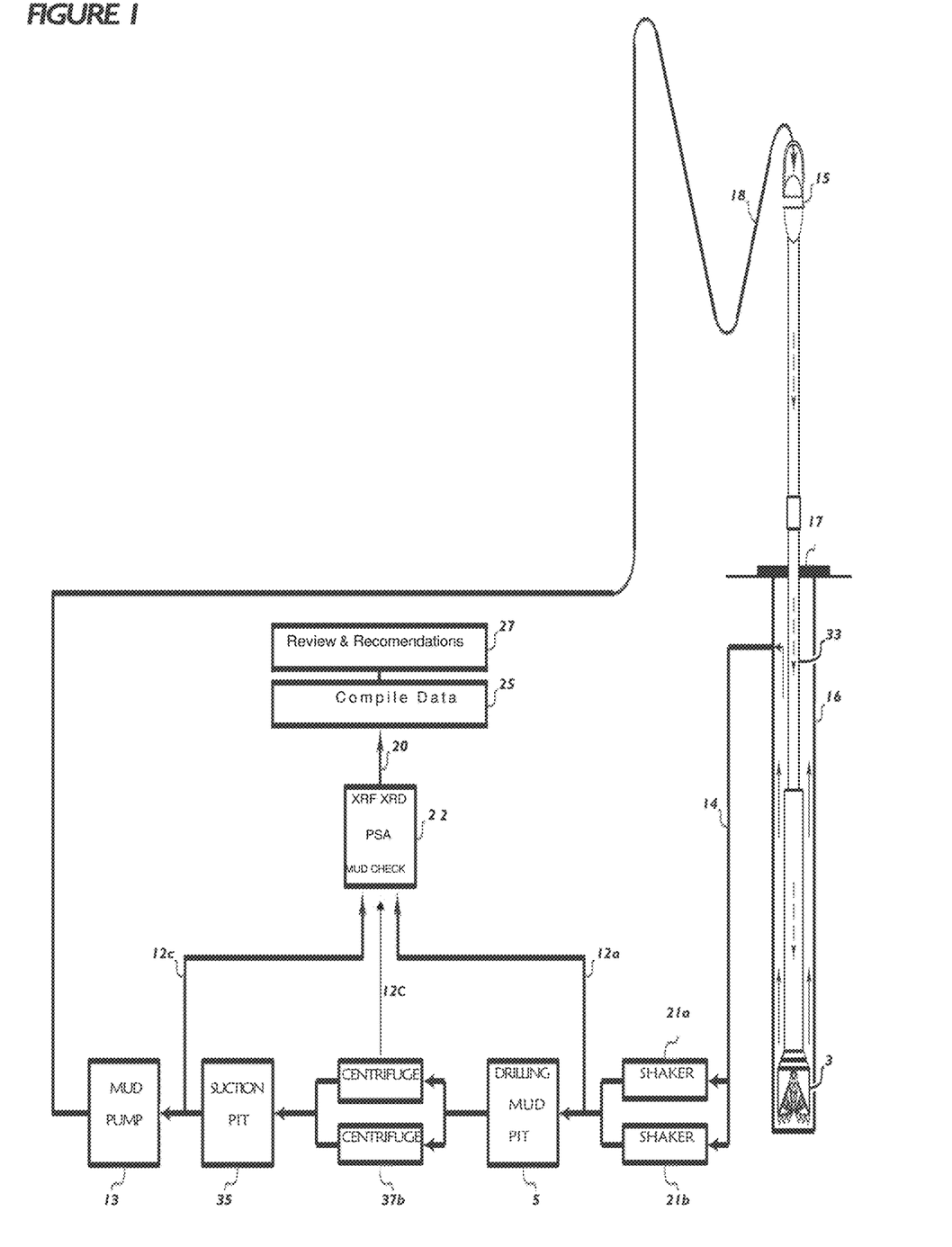
FIG. 1 is a diagram of drilling mud circulation for a wellbore and the equipment usable with the methods and systems.
Figure 2:
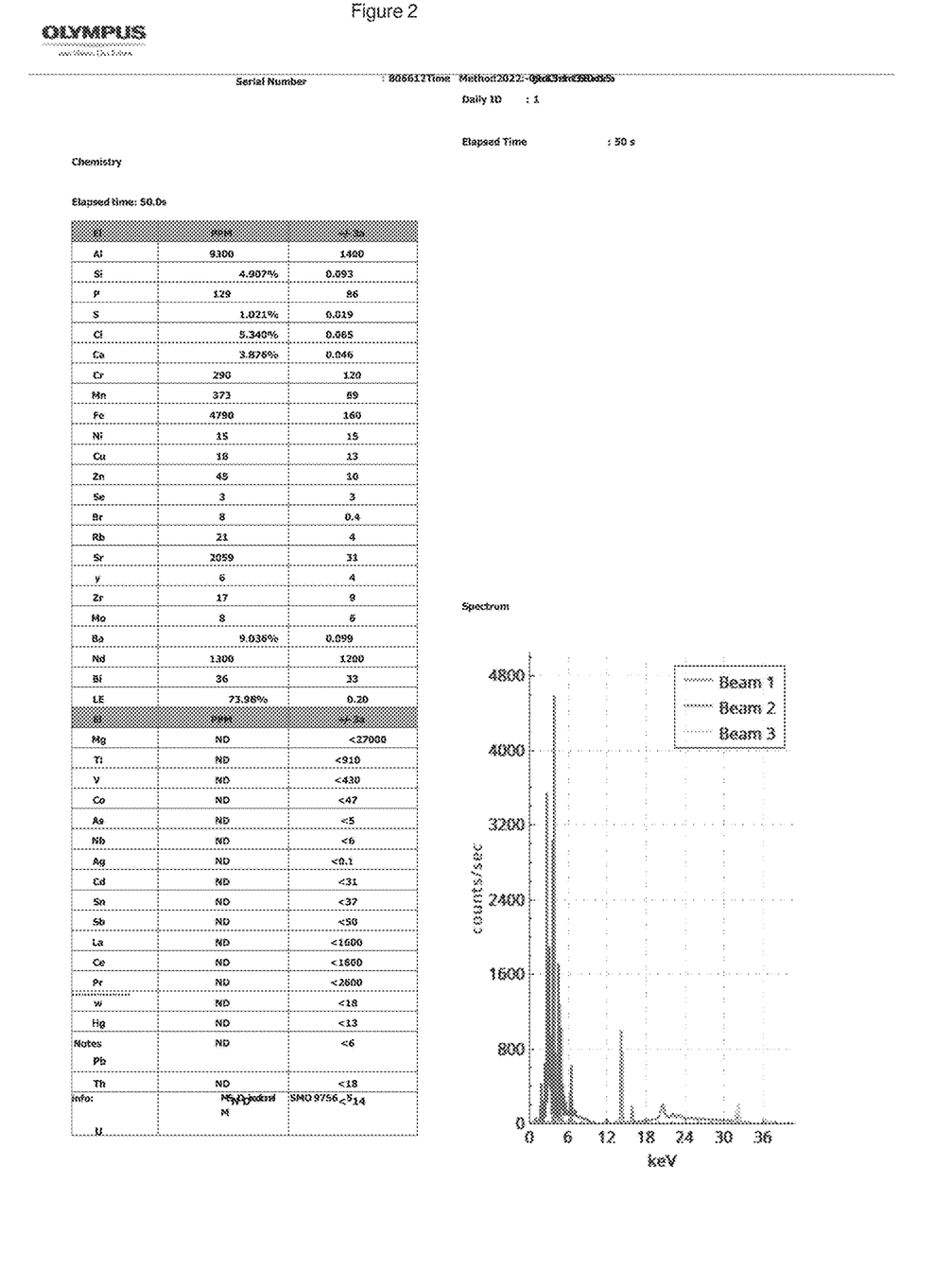
FIG. 2 is an example of an XRF elemental and compound analysis of a drilling fluid measure the elements/compounds of the abrasive formation materials within a drilling fluid, e.g., silicate ($SiO_2$), barite ($BaSO_4$), etc.
Figure 4:
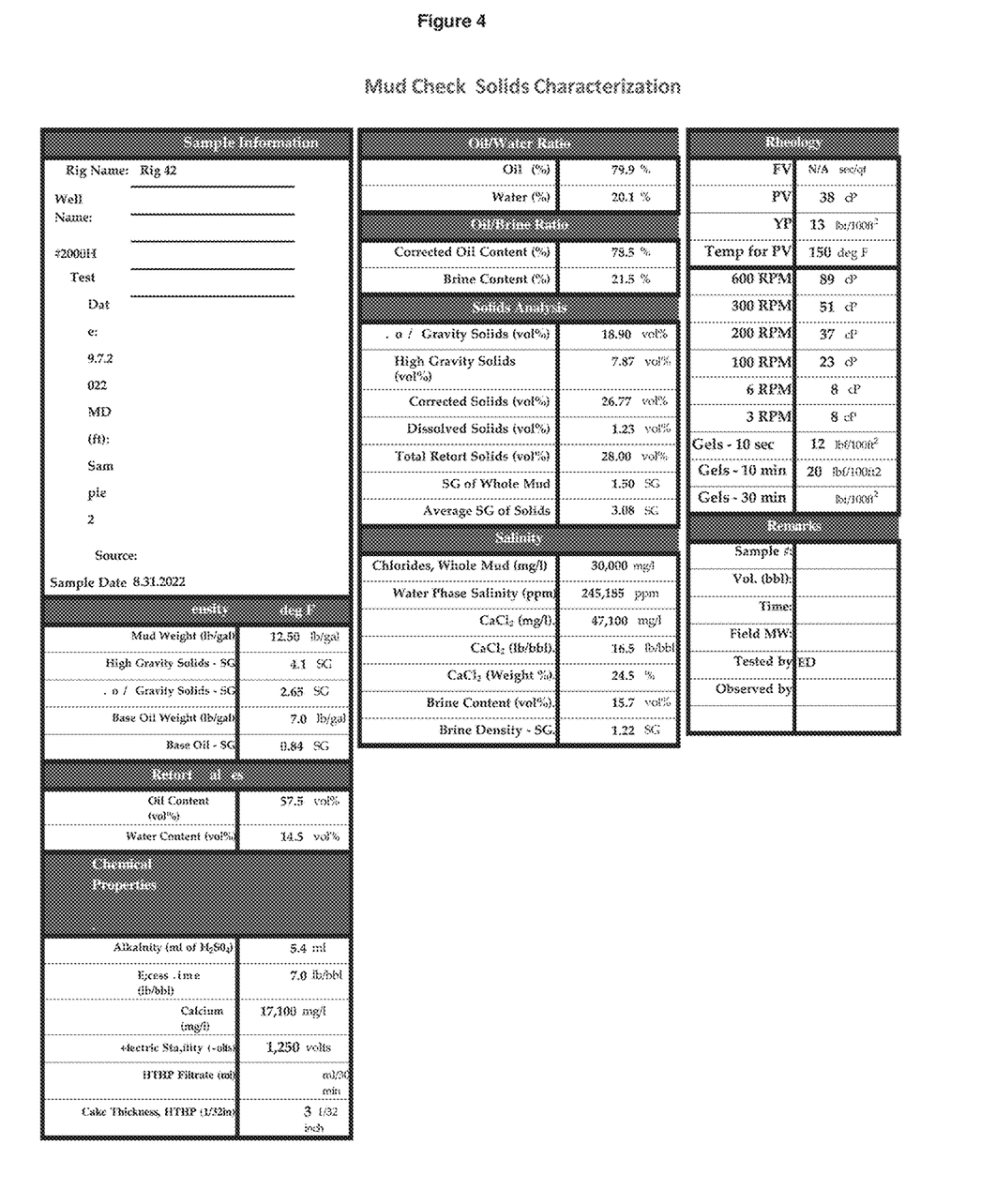
FIG. 4 is an example of a mud check performed on the drilling fluid that is going back downhole. Mud check identifies the properties of the drilling fluid and the percentage of formation and weighting material in the LGS and high-gravity solids ("HGS"), such as barite, that are used as a weighting material.
Figure 5:
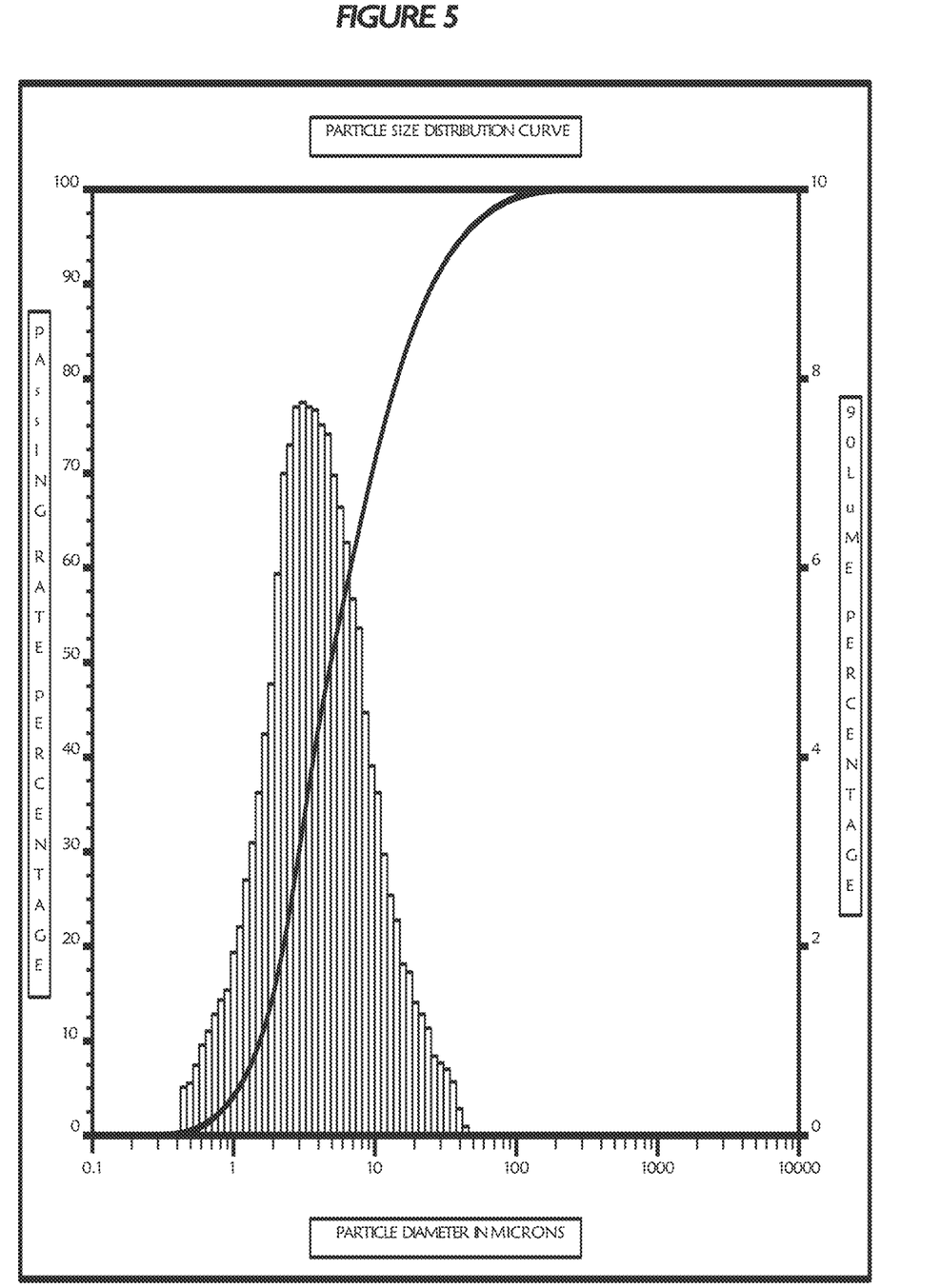
FIG. 5 is an example of a particle-size distribution curve for a drilling mud sample that has been optimized to reduce the amount of LGS and reduction in LGS solids along with a reduction in abrasive formation material (i.e., also referred to herein as "formation material" sometimes) that causes wear and abrasion on the surface and downhole tools.

Turning now to the figures, FIG. 1 is a diagram of drilling mud circulation for a wellbore and exemplary equipment usable with the disclosed methods and systems.

In one example embodiment, cleaned drilling mud 18 is piped from a suction pit 35 by a mud pump 13 to a swivel 15 connected to a kelly bushing 17 for then entering drill pipe 33 that is run into a wellbore 16. The cleaned drilling mud 18 flows down the wellbore to a drill bit 3.

Used drilling mud 14 is pulled back out of the wellbore and a plurality of drilling mud samples 12a-12c are then analyzed by the methods and systems to produce analyses by XRF, XRF, PSA and a Mud Check that provide and present drilling mud particle size, elemental and formation material analysis after different stages of cleaning, by shaker and by centrifuge. After shaking and cleaning, the cleaned drilling mud 18 is then returned to the wellbore.

More specifically, the mud from the shakers 21a and 21b is mixed together and the drilling mud sample 12a is taken out of the drilling mud line.

The drilling mud sample 12b is taken after treatment by the shakers 21a and 21b, and centrifuges 37a and 37b.

In embodiments a drilling mud pit 5 can be positioned between the shakers and the centrifuge and the drilling mud sample 12b can pass through the drilling mud pit 5 as well.

The drilling mud sample 12c is taken after the shakers 21a and 21b, the centrifuges 37a and 37b and a suction pit 35.

The shakers, centrifuges and suction pit are part of the processes for cleaning the drilling mud as moved by the mud pumps.

The particle size analyzer 22 may receive and analyze the drilling mud samples 12a-12c. The particle size analyzer produces data 20 which includes producing particle-size distribution curves for each of the plurality of drilling mud samples 12a-12c.

The x-ray fluorescence and x-ray diffraction equipment, also known as analyzer 22, may receive and analyze the drilling mud sample(s) 12a-12c. The x-ray fluorescence and x-ray diffraction analyzer produce data 20, which includes identification of formation element analysis via the x-ray fluorescence and specific percentage of formation material via the x-ray diffraction to provide percent of LGS and elemental analyses of the drilling fluid by the drilling mud sample(s) 12a-12c.

In example embodiments, the methods' and systems' particle-size analyzer measures sequentially, or even one or more simultaneously, a plurality of drilling mud sample(s) 12a-12c from the used drilling mud 14 from the wellbore 16.

The particle size distribution curve depicts the size of particles in the drilling mud sample against a passing rate percent. The methods may include plotting a particle diameter in at least one drilling mud sample against a passing rate percentage for particle sizes in the at least one drilling mud sample, and/or plotting a particle diameter in at least one drilling mud sample against a volume percentage passing for particle sizes in the at least one drilling mud sample. The methods' and systems' plotting of the particle size distribution curve may include plotting a volume distribution curve and/or a percent passing curve.

The term "passing rate percent" as used herein refers to a percent of particles smaller than a preset diameter contained in the drilling mud sample.

The particle size distribution curve depicts a percent volume in the drilling mud sample. The term "percent volume" as used herein refers to a percent of volume of particles that match a specific size diameter.

The data, which can include information for generating particle size distribution curves, and XRF data can be sent to an administrative processor with the XRD and XRF elemental percentage against true vertical and measured depth.

EXAMPLES

The XRF and or XRD showed in FIGS. 2-5 contain an excessive amount of undesirable particulate, i.e., abrasive formation material(s), e.g., quartz or sand, which is abrasive, such as determined by an operator based on mud weight and volume of abrasive material derived from an analysis by XRD for specific formation materials.

Based on this analysis, the disclosed methods and systems recommend, through enabling logic reduced to software and/or hardware, one, two, three, four, or simply one or more corrective action(s) to correct or mitigate these causes: (i) increasing rotations per minute on a centrifuge; (ii) increasing g-force on a centrifuge; (iii) increasing retention time of solids within a centrifuge; and (iv) diluting centrifuge feed with base fluid to lower the abrasive formation mineral(s) causing abrasive wear. In addition, the enabling logic may provide other corrective action(s) for improving the quality of the drilling mud under analysis.

These steps may be repeated until at least meeting a threshold that the particle size distribution no longer contains: (a) an excessive amount of formation mineral within low gravity solids; and/or (b) a specific mineral. Enabling logic, reduced to software and/or hardware, locally and/or remotely associated with the methods and systems enable an administrator, user or and/or both or otherwise to set a default setting or a configurable setting until at least meeting a threshold for: (i) number of iterations; (ii) size, weight, and/or hardness of the abrasive formation material(s) in the particle size distribution to prevent another iteration; (iii) average maximum for size, weight, and/or hardness of the abrasive formation material(s) in the particle size distribution to prevent another iteration, or (iv) combinations thereof.

Enhancements to the disclosed methods and systems may use artificial intelligence to provide a closed loop, automated system for analyzing and obtaining the unique particle size distribution curve through the solids control equipment used in normal operation on a drilling rig along with automatically modifying the mud properties, e.g., density, viscosity, plastic viscosity, yield point, salinity, chlorinity, alkalinity, electric stability, hardness, gel strength, oil/water ratio, corrected solids, total solids, and cake thickness.

In various embodiments, the methods and systems may have an automated knowledge-based system for rig personnel or other users to improve the operation in a timelier manner to maintain the proper particle size distribution.

In various embodiments, the equipment used in the methods and systems may be installed on a drilling rig and will allow for the continuous monitoring of the XRF, XRD particle size distribution curve within the drilling fluid being transported down the drill bit to arrive at the drill bit in order to increase the efficiency between the drill bit and the formation, lubricate the drill bit and minimize abrasive wear on downhole tools.

Figure 6:
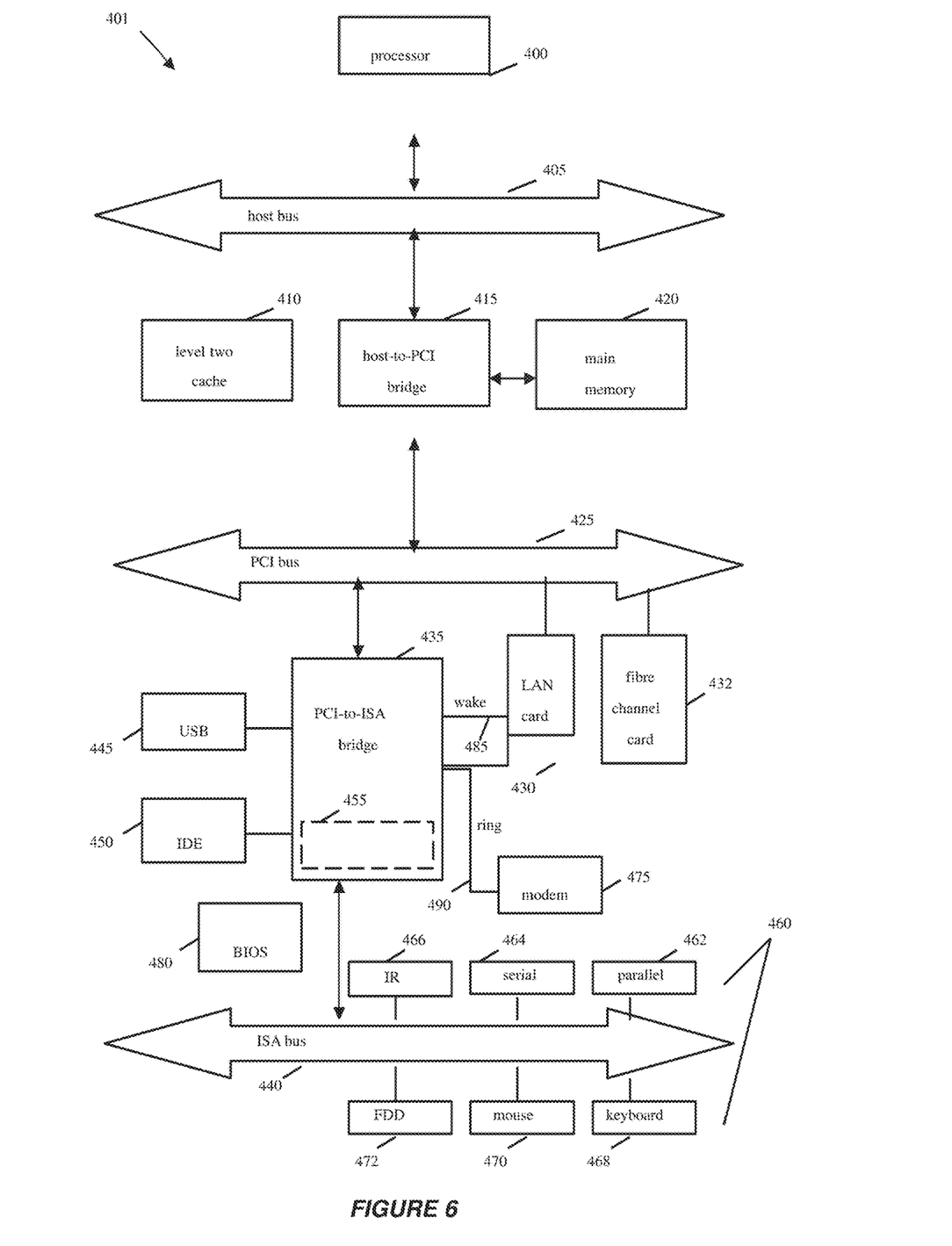
FIG. 6 is an example embodiment of an information handling system, which is a simplified example of a computer system in communication with a networked system computer capable of performing the operations described herein.

FIG. 6 illustrates an information handling system 401, which is a simplified example of a computer system in communication with a networked system computer, capable of performing the operations described herein. Computer system 401 includes processor 400 which is coupled to host bus 405. A level two (L2) cache memory 410 is also coupled to the host bus 405. Host-to-PCI bridge 415 is coupled to main memory 420, includes cache memory and main memory control functions, and provides bus control to handle transfers among PCI bus 425, processor 400, L2 cache 410, main memory 420, and host bus 405. PCI bus 425 provides an interface for a variety of devices including, for example, LAN card 430. PCI-to-ISA bridge 435 provides bus control to handle transfers between PCI bus 425 and ISA bus 440, universal serial bus (USB) functionality 445, IDE device functionality 450, power management functionality 455, and can include other functional elements not shown, such as a real-time clock (RTC), DMA control, interrupt support, and system management bus support. Peripheral devices and input/output (I/O) devices can be attached to interfaces 460 (e.g., parallel interface 462, serial interface 464, infrared (IR) interface 466, keyboard interface 468, mouse interface 470, fixed disk (HDD) 472, removable storage device 474) coupled to ISA bus 440. Alternatively, many I/O devices can be accommodated by a super I/O controller (not shown) attached to ISA bus 440.

BIOS 480 is coupled to ISA bus 440, and incorporates the necessary processor executable code for a variety of low-level system functions and system boot functions. BIOS 480 can be stored in any computer-readable storage medium, including magnetic storage media, optical storage media, flash memory, random access memory, read only memory, and so forth. In order to attach computer system 401 to another computer system to copy files over a network, LAN card 430 is coupled to PCI bus 425 and to PCI-to-ISA bridge 435. Similarly, to connect computer system 401 to an ISP to connect to the Internet using a telephone line connection, modem 475 is connected to serial port 464 and PCI-to-ISA Bridge 435.

While the computer system described in FIG. 6 is capable of executing the disclosure described herein, this computer system is simply one example of a computer system. Those skilled in the art will appreciate that many other computer system designs are capable of performing the disclosure described herein.

Another embodiment of the disclosure is implemented as a program product for use within a device such as, for example, those systems and methods depicted in FIGS. 1-5. The program(s) of the program product defines functions of the embodiments (including the methods described herein) and can be contained on a variety of data-bearing media. Illustrative data-bearing media include, but are not limited to: (i) information permanently stored on non-writable storage-type accessible media (e.g., read-only memory devices within a computer such as CD-ROM disks readable by a CD-ROM drive); (ii) alterable information stored on writable storage-type accessible media (e.g., floppy disks within a diskette drive or hard-disk drive); and (iii) information conveyed to a computer by a communications medium, such as through a computer or telephone network, including wireless communications. The latter embodiment specifically includes information downloaded onto either permanent or even sheer momentary storage-type accessible media from the World Wide Web, an internet, and/or other networks, such as those known, discussed and/or explicitly referred to herein. Such data-bearing media, when carrying computer-readable instructions that direct the functions of the present disclosure, represent embodiments of the present disclosure.

In general, the routines executed to implement the embodiments of this disclosure, may be part of an operating system or a specific application, component, program, module, object, or sequence of instructions. The computer program of the present disclosure typically is comprised of a multitude of instructions that will be translated by the native computer into a machine-readable format and hence executable instructions. Also, programs are comprised of variables and data structures that either reside locally to the program or are found in memory or on storage devices. In addition, various programs described hereinafter may be identified based upon the application for which they are implemented in a specific embodiment of this disclosure. However, it should be appreciated that any particular program nomenclature that follows is used merely for convenience, and thus this disclosure should not be limited to use solely in any specific application identified and/or implied by such nomenclature.

Below are further example embodiments of the disclosed methods and systems that are written in a shortened claim format but each may be re-written in paragraph form and are to be understood as such and are a part of this detailed description as much as any other part.

1. A method on a drilling fluid comprising:
   acquiring data from each of a particle-size analyzer, x-ray fluorescence instrument, a mud check, and optionally an x-ray diffraction instrument, to yield acquired data for each of a plurality of drilling mud samples, wherein:
   the particle size analyzer measures a plurality of drilling mud samples from the drilling mud, the x-ray fluorescence instrument and the x-ray diffraction instrument measure a mineral analysis of the plurality of drilling mud samples from the drilling mud, the mud check measures properties of the plurality of drilling mud samples from the drilling mud, plotting, based on the acquired data, a particle size distribution curve for at least one of the plurality of drilling mud samples;

calculating, based on the acquired data, an amount of abrasive formation material(s) within at least one of the plurality of drilling mud samples; and adjusting, based at least on the plotting and calculating, the drilling fluid.

2. The method of claim 1, wherein the plotting comprises plotting a particle diameter in at least one drilling mud sample against a passing rate percentage for particle sizes in the at least one drilling mud sample.

3. The method of claim 1, wherein the plotting comprises plotting a particle diameter in at least one drilling mud sample against a volume percentage passing for particle sizes in the at least one drilling mud sample.

4. The method of claim 1, wherein the plotting the particle size distribution curve comprises plotting a volume distribution curve and a percent passing curve.

5. The method of claim 1, wherein the particle sizer analyzer measures each of the plurality sequentially.

6. The method of claim 1, wherein the particle sizer analyzer measures each of the plurality simultaneously.

7. The method of claim 1, wherein the calculating further comprises calculating a volume of sand per barrel within at least one of the plurality of drilling mud samples, and a rate of the sand being passed through surface and downhole drilling equipment.

8. The method of claim 1, wherein the method performs the plotting, the calculating, and the adjusting for each of the plurality.

9. The method of claim 1, wherein the adjusting comprises adjusting at least one particulate removal device to remove an undesirable particulate from the drilling mud.

10. The method of claim 1, wherein the adjusting comprises diluting to remove an undesirable particulate from the drilling mud, wherein the undesirable particulate comprises the abrasive formation material(s).

11. The method of claim 1, wherein the method further comprises recommending at least one of: (i) increasing rotations per minute on a centrifuge; (ii) increasing g-force on a centrifuge; (iii) increasing retention time of solids within a centrifuge; and (iv) diluting centrifuge feed with base fluid to lower the abrasive formation mineral(s).

12. The method of claim 1, wherein the method further comprises recommending at least one or more corrective actions.

13. The method of claim 1, wherein the method further comprises, subsequent to the acquiring, the plotting and the calculating, recommending more than one corrective actions.

14. The method of claim 1, wherein the method further comprises iterating the method.

15. The method of claim 1, wherein the method further comprises iterating the method until at least meeting a threshold for: (i) number of iterations; (ii) size, weight, and/or hardness of the abrasive formation material(s) in the particle size distribution to prevent another iteration; (iii) average maximum for size, weight, and/or hardness of the abrasive formation material(s) in the particle size distribution to prevent another iteration, or (iv) combinations thereof.

16. The method of claim 1, wherein the method further comprises iterating the method until at least meeting a threshold that the particle size distribution no longer contains an excessive amount of one or more of the abrasive formation material(s).

17. The method of claim 1, wherein the method further comprises iterating the method until at least meeting a threshold that the particle size distribution no longer contains an excessive amount of sand.

18. The method of claim 14, wherein the threshold is configurable.

19. The method of claim 15, wherein the threshold is configurable.

20. The method of claim 1, wherein the method further comprises the x-ray diffraction instrument and the acquired data comprises data therefrom.

21. The method of claim 1, wherein one or more steps in the method are computer-implemented, enabled instructions having access to the acquired data and executed by an associated processor.

22. The method of claim 1, wherein the method further comprises any combination of the foregoing claims 1-21 or portions thereof.

While the foregoing is directed to example embodiments of the disclosed invention, other and further embodiments may be devised without departing from the basic scope thereof, wherein the scope of the disclosed systems and methods are determined by one or more claims.

What is claimed is:

1. A method performed on a drilling fluid comprising:

receiving the drilling fluid by a system, wherein the system is in communication with instrumentation for:

acquiring data from each of: (i) a particle-size analyzer, (ii) x-ray fluorescence instrument, and (iii) a mud check, to yield acquired data for each of a plurality of drilling fluid samples, wherein:

the particle size analyzer measures a plurality of drilling fluid samples from the drilling fluid, the x-ray fluorescence instrument and the x-ray diffraction instrument measure a mineral analysis of the plurality of drilling fluid samples from the drilling fluid, the mud check measures properties of the plurality of drilling fluid samples from the drilling fluid, determining sizes of particles for at least one of the plurality of drilling fluid samples;

calculating, based on the acquired data, an amount of abrasive formation material(s) within at least one of the plurality of drilling fluid samples, including calculating a volume of sand per barrel within at least one of the plurality of drilling fluid samples, and a rate of the sand being passed through surface and downhole drilling equipment;

adjusting, based at least on the determining and the calculating, the drilling fluid to remove a portion of the amount, whereby performing the method using the drilling fluid without the portion yields at least a 20% improvement in drilling operations and reduces wear on downhole tools, pipes, elastomers, and/or other mechanical mechanisms as compared to using the drilling fluid with the amount in the drilling operations with all other variables constant; and collecting, at least a portion of the drilling fluid adjusted by the method, in a suction pit or other container in communication with the system.

2. The method of claim 1, wherein the determining the particle size distribution curve comprises plotting a volume distribution curve and a percent passing curve.

3. The method of claim 1, wherein the particle sizer analyzer measures each of the plurality sequentially.

4. The method of claim 1, wherein the particle sizer analyzer measures each of the plurality simultaneously.

5. The method of claim 1, wherein the adjusting comprises adjusting at least one particulate removal device to remove at least some of the portion.

6. The method of claim 1, wherein the adjusting comprises diluting to remove at least some of the portion of an undesirable particulate from the drilling fluid.

7. The method of claim 1, wherein the method further comprises recommending at least one of: (i) increasing rotations per minute on a centrifuge; (ii) increasing g-force on a centrifuge; (iii) increasing retention time of solids within a centrifuge; and (iv) diluting centrifuge feed with base fluid to lower the abrasive formation mineral(s).

8. The method of claim 1, wherein the method further comprises recommending at least one or more corrective actions.

9. The method of claim 1, wherein the method further comprises iterating the method until at least meeting a threshold for: (i) number of iterations; (ii) size, weight, and/or hardness of the abrasive formation material(s) in the particle size distribution to prevent another iteration; (iii) average maximum for size, weight, and/or hardness of the abrasive formation material(s) in the particle size distribution to prevent another iteration, or (iv) combinations thereof.

10. The method of claim 1, wherein the method further comprises iterating the method until at least meeting a threshold that the particle size distribution no longer contains at least the portion.

11. The method of claim 1, wherein the method further comprises the x-ray diffraction instrument and the acquired data comprises data therefrom.

12. The method of claim 1, wherein the adjusting comprises diluting the drilling fluid.

13. The method of claim 1, wherein the portion comprises quartz.

14. The method of claim 1, wherein the portion comprises sand.

15. The method of claim 1, wherein the calculating comprises calculating with the x-ray diffraction instrument.

16. The method of claim 1, wherein the calculating comprises calculating with the x-ray fluorescence instrument.

17. The method of claim 1, wherein the adjusting also reduces non-productive time as compared to using the drilling fluid with the amount in the drilling operations with all other variables constant.

18. The method of claim 1, further comprising monitoring the particle size distribution curve within the drilling fluid.

19. The method of claim 1, wherein the particle-size analyzer, the x-ray fluorescence instrument, the mud check, and optionally the x-ray diffraction instrument are located on a drilling rig.

20. The method of claim 1, wherein the performing the method occurs in real time or near-real time with the drilling operations.

21. The method of claim 1, further comprising returning, subsequent to the collecting, at least some of the at least a portion of the drilling fluid to the system.

22. The method of claim 1, further comprising receiving, subsequent to the collecting, at least some of the at least a portion of the drilling fluid, by a drill pipe.

23. The method of claim 1, wherein the system comprises a well bore having at least some of the at least a portion of the drilling fluid adjusted by the method.

24. A method performed on a drilling fluid comprising:
receiving the drilling fluid by a system, wherein the system is in communication with instrumentation for:
acquiring data from each of: (i) x-ray fluorescence instrument, (ii) optionally an x-ray diffraction instrument, and (iii) optionally a mud check, to yield acquired data for each of a plurality of drilling fluid samples, wherein:
the x-ray fluorescence instrument and the x-ray diffraction instrument measure a mineral analysis of the plurality of drilling fluid samples from the drilling fluid,
the mud check measures properties of the plurality of drilling fluid samples from the drilling fluid,
calculating, based on the acquired data, an amount of abrasive formation material(s) within at least one of the plurality of drilling fluid samples, including calculating a volume of sand per barrel within at least one of the plurality of drilling fluid samples, and a rate of the sand being passed through surface and downhole drilling equipment;
adjusting, based at least on the calculating, the drilling fluid to remove a portion of the amount, whereby performing the method using the drilling fluid without the portion yields at least a 20% improvement in drilling operations and reduces wear on downhole tools, pipes, elastomers, and/or other mechanical mechanisms as compared to using the drilling fluid with the amount in the drilling operations with all other variables constant; and
collecting, at least a portion of the drilling fluid adjusted by the method, in a suction pit or other container in communication with the system.

25. The method of claim 23, wherein the calculating and adjusting is based only on the acquired data from the x-ray fluorescence instrument.

26. The method of claim 1, wherein the acquiring the data further comprises from: (iv) an x-ray diffraction instrument, wherein (i)-(iv) yield the acquired data.

* * * * *